United States Patent
Poole et al.

(10) Patent No.: US 7,399,296 B2
(45) Date of Patent: Jul. 15, 2008

(54) CATHETER HAVING HIGHLY RADIOPAQUE EMBEDDED SEGMENT

(75) Inventors: Matthew S. Poole, Bradford, MA (US); Eliza K. Stepp, Cambridge, MA (US); Zelda M. Anastos, Brighton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 766 days.

(21) Appl. No.: 10/374,610

(22) Filed: Feb. 26, 2003

(65) Prior Publication Data

US 2004/0167496 A1    Aug. 26, 2004

(51) Int. Cl.
  *A61M 25/098*    (2006.01)
(52) U.S. Cl. .................................... 604/529
(58) Field of Classification Search ........ 604/529–531, 604/524, 264
  See application file for complete search history.

(56) References Cited

U.S. PATENT DOCUMENTS

| | | | |
|---|---|---|---|
| 4,027,659 A | 6/1977 | Slingluff | |
| 4,629,451 A | 12/1986 | Winters et al. | |
| 4,657,024 A * | 4/1987 | Coneys | 600/435 |
| 4,796,637 A | 1/1989 | Mascuch et al. | |
| 4,938,220 A | 7/1990 | Mueller | 600/435 |
| 5,045,071 A | 9/1991 | McCormick et al. | 604/529 |
| 5,112,304 A * | 5/1992 | Barlow et al. | 604/103.09 |
| 5,147,315 A * | 9/1992 | Weber | 604/164.09 |
| 5,318,032 A * | 6/1994 | Lonsbury et al. | 600/435 |
| 5,630,806 A * | 5/1997 | Inagaki et al. | 604/524 |
| 5,676,659 A * | 10/1997 | McGurk | 604/527 |
| 5,728,065 A * | 3/1998 | Follmer et al. | 604/96.01 |
| 5,766,202 A * | 6/1998 | Jones et al. | 606/196 |
| 5,858,556 A * | 1/1999 | Eckert et al. | 428/586 |
| 5,908,413 A * | 6/1999 | Lange et al. | 604/529 |
| 6,024,722 A * | 2/2000 | Rau et al. | 604/96.01 |
| 6,042,578 A | 3/2000 | Dinh et al. | |
| 6,059,769 A | 5/2000 | Lunn et al. | |
| 6,171,297 B1 | 1/2001 | Pederson et al. | 604/527 |
| 6,174,329 B1 | 1/2001 | Callol et al. | |
| 6,213,995 B1 * | 4/2001 | Steen et al. | 604/527 |
| 6,221,059 B1 | 4/2001 | Chiang et al. | 604/264 |
| 6,503,353 B1 | 1/2003 | Peterson et al. | 156/86 |

(Continued)

FOREIGN PATENT DOCUMENTS

WO    WO91/04068    4/1991

(Continued)

OTHER PUBLICATIONS

Spurlock, J.P., et al., "A caprine breast model for testing a novel balloon brachytherapy device," Online J. Vet. Res. (2000) 4:106-123.

*Primary Examiner*—Manuel A Mendez
(74) *Attorney, Agent, or Firm*—James F. Crittenden

(57) ABSTRACT

Medical catheters adapted for use within a body vessel and methods of manufacturing are presented herein. The medical catheter comprises a tubular catheter shaft having a distal end that fits within the body vessel. The tubular catheter shaft comprises an unfilled or low-loaded inner liner and/or outer shell. The medical catheter also comprises a radiopaque segment that comprises a radiopaque material embedded between the inner liner and outer shell. The radiopaque material can be in the form of an ink, powder, or paste.

7 Claims, 3 Drawing Sheets

U.S. PATENT DOCUMENTS

| | | | |
|---|---|---|---|
| 6,508,784 B1 * | 1/2003 | Shu | 604/96.01 |
| 6,574,497 B1 | 6/2003 | Pacetti | |
| 6,591,472 B1 * | 7/2003 | Noone et al. | 29/417 |
| 6,635,047 B2 * | 10/2003 | Forsberg | 604/526 |
| 6,641,776 B1 * | 11/2003 | Weaver et al. | 264/642 |
| 6,648,854 B1 * | 11/2003 | Patterson et al. | 604/96.01 |
| 6,652,568 B1 * | 11/2003 | Becker et al. | 623/1.11 |
| 2001/0003297 A1 | 6/2001 | Perdersen et al. | |
| 2003/0009150 A1 | 1/2003 | Pepin | |
| 2003/0009184 A1 | 1/2003 | Pepin | 606/159 |

FOREIGN PATENT DOCUMENTS

| | | |
|---|---|---|
| WO | WO99/48548 | 9/1999 |
| WO | 0043061 | 7/2000 |
| WO | WO01/95794 | 1/2001 |
| WO | WO02/39927 | 5/2002 |
| WO | 0304085 | 1/2003 |
| WO | WO03/97148 | 11/2003 |

* cited by examiner

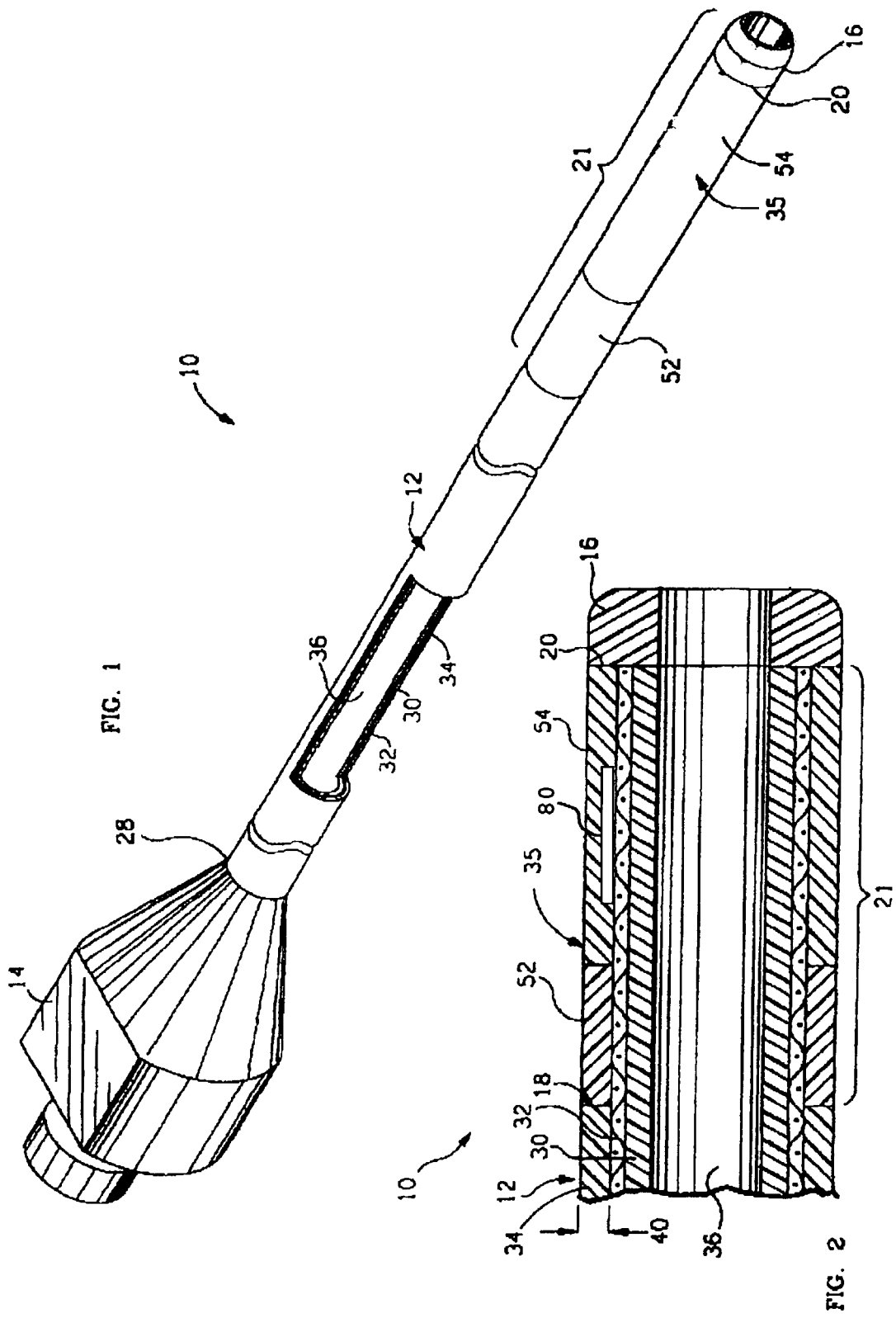

CATHETER HAVING HIGHLY RADIOPAQUE EMBEDDED SEGMENT

FIELD OF THE INVENTION

The present invention relates to a catheter comprising a radiopaque segment and a method of manufacturing such a catheter. More specifically, the present invention relates to a catheter having a highly radiopaque segment in the distal end portion.

BACKGROUND OF THE INVENTION

A number of intravascular procedures are currently utilized to treat a stenosis within a body vessel of a human being. A common intravascular procedure is referred to as percutaneous transluminal coronary angioplasty (hereinafter "angioplasty"). During a typical angioplasty procedure, a guidewire is initially positioned within the body vessel and a guiding catheter is positioned over the guidewire. Next, a balloon catheter having an inflatable balloon is advanced through the guiding catheter and vessel until the balloon is adjacent to the stenosis. Subsequently, inflation of the balloon compresses the stenosis and dilates the body vessel.

During many surgical and clinical procedures it is necessary to determine the location or position of the catheter within the body of the patient into which it has been inserted. One manner of locating the position of the catheter is to add a sufficient amount of a radiopacifying agent directly to the polymeric catheter materials. Alternatively, the use of filler material in the polymer itself may be minimized, while building in wires or selectively placing metal bands that are highly radiopaque (see, for example U.S. Pat. Nos. 4,657,024 and U.S. Pat. No. 4,796,637, each of which is incorporated herein by reference in its entirety). Use of these types of catheters, however, has drawbacks. The metal bands, for example, are inherently very stiff and generate undesirable transitions in the flexibility of the catheter shaft. In addition, radiopaque wires are more costly than the commonly used stainless steel and, for simplicity in fabrication, such wires typically extend the full length of the device.

Thus, there is a need to develop a catheter that is easily visualized during its use in a patient without sacrificing the flexibility that is important during the use of the catheter. Similarly, there is a need for a catheter that may be visualized without substantially increasing the cost. A catheter that is flexible and visible under fluoroscopy or x-ray will enable people in the medical community to better perform surgical and clinical procedures involving a catheter. The present invention is directed to these, as well as other, important needs.

SUMMARY OF THE INVENTION

The present invention is directed to medical catheters adapted for use within a body vessel. The medical catheter comprises a tubular catheter shaft having a distal end that fits within the body vessel. The tubular catheter shaft comprises an unfilled or low-loaded inner liner and/or outer shell. The medical catheter also comprises a radiopaque segment that comprises a radiopaque material embedded between the inner liner and outer shell. In one embodiment, the radiopaque material is in the form of an ink, powder, or paste.

In some embodiments, the radiopaque material comprises stainless steel, gold, tantalum, platinum, bismuth, iridium, zirconium, iodine, titanium, barium, silver, tin, tungsten, bromide, alloys of these materials, salts of these materials, or any combination thereof. In other embodiments, the radiopaque material comprises barium sulfate, bismuth trioxide, bismuth subcarbonate, a tantalum powder, or any combination thereof. In other embodiments, the radiopaque material comprises a ceramic, such as zirconia, alumina, zirconium nitrate, titanium nitrite, graphite, or pyrolytic carbon.

In one embodiment, at least one filament of a braid may comprise a radiopaque material. In another embodiment, the radiopaque segment is localized to the tip of the catheter. In another embodiment, the outer shell of the radiopaque segment comprises a material having properties that are different from those of the inner liner. In some embodiments, the inner liner and/or outer shell may be low-loaded, comprising between about 0.1% and about 10% of radiopaque material, filler, or colorant by weight. Alternatively, the inner liner and/or outer shell may be unfilled, comprising no amount of radiopaque material, filler, or colorant by weight.

The present invention is also directed to methods for making a medical catheter comprising providing a medical catheter having an outer shell, ablating a distal end portion of the catheter to remove a portion of the outer shell, applying a radiopaque material to the ablated distal end portion of the catheter, and applying material forming the outer shell over the radiopaque material within the ablated distal end portion of the catheter. The radiopaque material may be applied to the ablated portion of the catheter by various methods such as dipping, spraying, painting, electroplating, plasma vapor deposition, cathodic arc deposition, sputtering, laser welding or fusing, resistance welding, ion beam assisted deposition, ion implantation, pad printing, or any combination thereof.

The present invention is also directed to medical catheters comprising a radiopaque segment produced by a method comprising providing a medical catheter having an outer shell, ablating a distal end portion of the catheter to remove a portion of the outer shell, applying a radiopaque material to the ablated distal end portion of the catheter to form a radiopaque segment, and applying material forming the outer shell over the radiopaque material of the ablated distal end portion of the catheter.

BRIEF DESCRIPTION OF THE DRAWINGS

The novel features of this invention, as well as the invention itself, both as to its structure and methods of making, will be best understood from the accompanying drawings, taken in conjunction with the accompanying description, in which similar reference characters refer to similar parts, and in which:

FIG. 1 is a perspective view, in partial cutaway, of a medical catheter having features of the present invention;

FIG. 2 is an enlarged cutaway view of a portion of the medical catheter of FIG. 1;

DETAILED DESCRIPTION OF THE INVENTION

Figure 3:
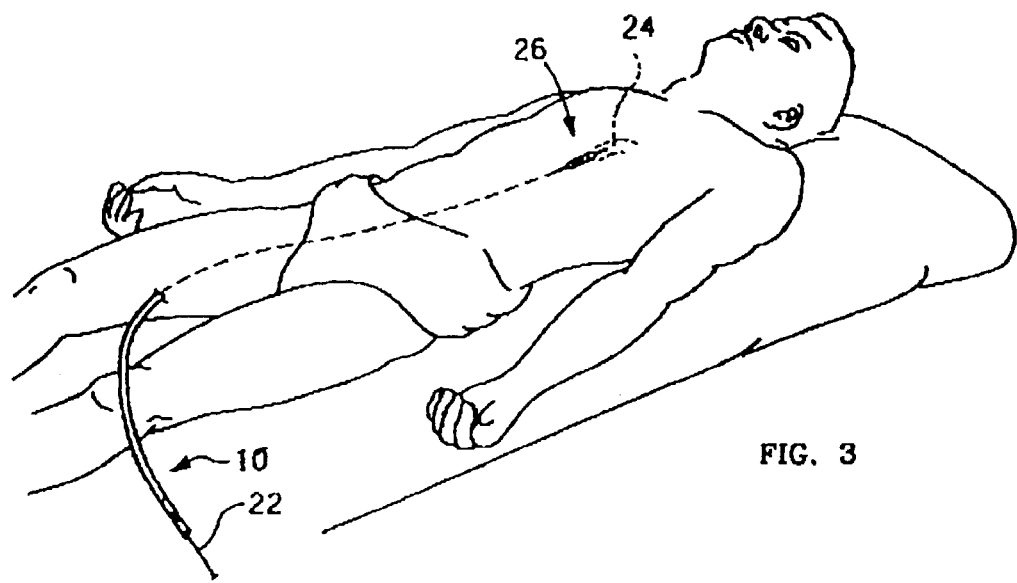
FIG. 3 is a perspective illustration of the medical catheter positioned within a patient.

The present invention is directed to a catheter having a distal end that comprises a radiopaque segment. Any medical catheter may be modified to comprise a radiopaque segment. Thus, the catheters described herein are merely exemplary and the invention should not be construed to be limited to only the catheters described herein. For example, referring to FIGS. 1, 2, and 4a, a first embodiment of a medical catheter 10 having features of the present invention includes a tubular catheter shaft 12, a hub 14, and a tubular flexible tip 16. The catheter shaft 12 may optionally include a groove 18, which is cut out of the catheter shaft 12 near a distal end 20 of the catheter shaft 12. The groove 18 provides flexibility at the distal end 20 of the catheter shaft 12 without compromising the durability and torsional strength of the catheter shaft 12. Further, the groove 18 functions as a transitional region 21 between the relatively stiff catheter shaft 12 and the flexible tip 16. This reduces or prevents kinking and/or collapsing of the medical catheter 10. As a result thereof, the medical catheter 10 has improved tracking and movement in the vessel.

The medical catheter 10 illustrated herein is utilized to guide a balloon catheter (not shown) and is commonly referred to as a guiding catheter. FIG. 3 illustrates a portion of the medical catheter 10 and a guidewire 22 positioned in a body vessel 24 of a patient 26 during a procedure. The location of entry into the patient 26 and the location of the distal end 20 in the patient 26 are merely exemplary.

Referring back to FIGS. 1 and 2, the hub 14 is secured to a proximal end 28 of the catheter shaft 12 while the flexible tip 16 is secured to the distal end 20 of the catheter shaft 12. The hub 14 and proximal end 28 are manipulated by the physician to position the medical catheter 10 in the body vessel 24. The flexible tip 16 assists in guiding the medical catheter 10 in the body vessel 24 and minimizes the trauma to the vessel 24 and coronary ostium (not shown).

The flexible tip 16 is made of a relatively soft material when compared to the catheter shaft 12. Suitable materials for the flexible tip 16 include polymers such as a polyether block amide ("PEBA") having a hardness of about 40 D. As used throughout the present description, the term "about" means ±5% of the value being modified (e.g., about 100 means 95 to 105). Depending upon the materials utilized, the hub 14 and the flexible tip 16 may be thermally bonded or attached with an adhesive (not shown) to the catheter shaft 12. Those skilled in the art will recognize alternate ways to attach the hub 14 and flexible tip 16 and that alternate materials may be utilized for the flexible tip 16.

In the embodiments illustrated in FIGS. 1 and 2, the tubular catheter shaft 12 includes an inner liner 30, an optional reinforcing section 32, and an outer shell 34. Further, when the catheter comprises a groove 18, a fill section 35 is positioned in the groove 18. The inner liner 30 is tubular and defines a guidewire lumen 36, which is sized and shaped to receive the guidewire 22 and subsequently a balloon catheter (not shown). Typically, the inner liner 30 is manufactured by extruding a polymer such as PEBA or nylon, which provides good flexibility and movement over the guidewire 22. A suitable inner liner 30 has an inner diameter of between about 0.08 and about 0.09 inches and an inner liner thickness of about 1.5 mils. In some embodiments, a coating (not shown) may be added to the guidewire lumen 36 of the inner liner 30 to facilitate movement of the inner liner 30 over the guidewire 22 and the balloon catheter within the guidewire lumen 36.

The optional reinforcing section 32 enhances the torsional strength and prevents or reduces kinking of the catheter shaft 12 during movement of the medical catheter 10 in the body vessel 24. The reinforcing section 32 is positioned between the inner liner 30 and the outer shell 34 and is substantially coaxial with the inner liner 30 and the outer shell 34. The reinforcing section 32 may be formed by braiding wire mesh around the inner liner 30. Subsequently, the outer shell 34 is formed around the reinforcing section 32 by applying materials making up the outer shell. An example of a suitable wire for braiding may be stainless steel, which is rolled flat and spring tempered.

The outer shell 34 provides support to the catheter shaft 12 and covers the reinforcing section 32 to protect the body vessel 24 from the reinforcing section 32. Further, the outer shell 34 prevents the reinforcing section 32 from unwrapping. The outer shell 34 is tubular and coaxial with the inner liner 30 and the reinforcing section 32. An example of a suitable outer shell 34 is one that has an inner diameter of about 0.1 inches and a shell thickness 40 of about 2.5 mils.

Typically, the outer shell 34 is manufactured by extruding a polymer over the reinforcing section 32. A suitable shell material for the outer shell 34 is a nylon sold under the trademark "TROGAMID" by Creanova (Somerset, N.J.). The shell material may have a hardness of about 81 D. Additionally, a lubricious coating (not shown) may be added to the outer shell 34 to facilitate movement of the catheter shaft 12 within the vessel 24.

Those skilled in the art will recognize alternate ways to manufacture the inner liner 30, the reinforcing section 32, and the outer shell 34, and that alternate materials can be utilized for the inner liner 30, the reinforcing section 32, and the outer shell 34.

The optional groove 18 is positioned near the distal end 20 of the catheter shaft 12 to provide flexibility in the transitional region. The size and shape of the groove 18 may be varied to suit the flexibility needs of the medical catheter 10. For example, a deeper and longer groove 18 provides increased flexibility but reduced torsional strength.

Figure 4A:
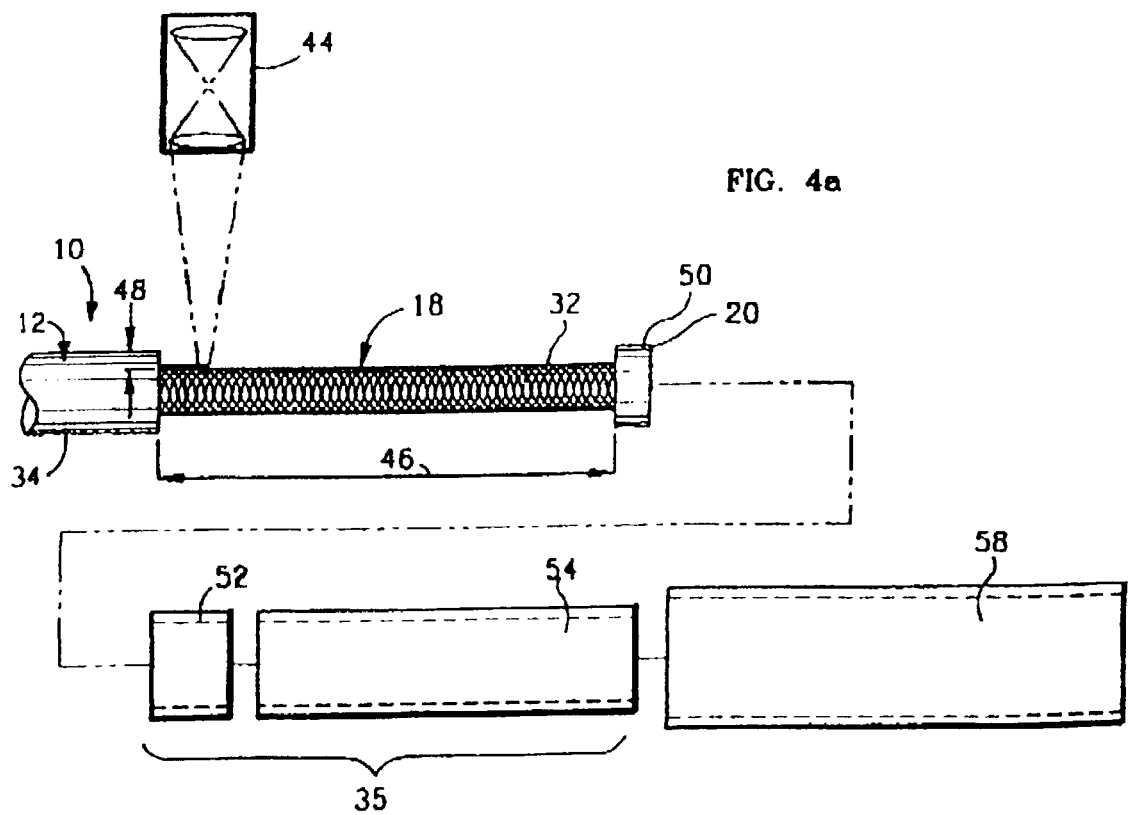
FIG. 4a is an enlarged side plan assembly view of a portion of the catheter shaft illustrating a groove, a fill section and a sleeve.

FIG. 4a illustrates a portion of one embodiment of a catheter shaft 12 having features of the present invention. In this embodiment, an annular shaped, circumferentially extending groove 18 has been formed in the outer shell 34 with a removing device 44. More specifically, the groove 18 illustrated in FIG. 4a has a groove length 46 of about three centimeters and a groove depth 48 of about 2.5 mils. In this embodiment, the groove depth 48 is about equal to the shell thickness of the outer shell 34. This exposes the reinforcing section 32 and allows the fill section 35 to be bonded directly to the reinforcing section 32. However, the groove depth 48 and groove length 46 can be varied to change the flexibility and torsional strength of the catheter shaft 12 near the distal end 20.

The groove 18 is formed near the distal end 20 of the catheter shaft 12. In some embodiments, a tubular remaining shell segment 50 may be positioned between the distal end 20 and the groove 18 after formation of the groove 18. The remaining shell segment 50 prevents the reinforcing section 32 from unwrapping.

The removing device 44 removes a portion of the outer shell 34 to form the groove 18. In some embodiments, the removing device 44 is an excimer laser that precisely removes a portion of the outer shell 34 to form the groove 18. The excimer laser allows a portion of the outer shell 34 to be removed without damaging the reinforcing section 32. Further, the excimer laser allows for the removal of the material embedded within the mesh of the reinforcing section 32. This will allow for a stronger bond between the fill section 35 and the reinforcing section 32.

Referring back to FIGS. 1 and 2, the fill section 35 can fill the groove 18 to provide continuity to the catheter shaft 12. The fill section 35 may have a hardness that is lesser than the hardness of a shell material utilized for the outer shell 34. This allows the fill section 35 to provide flexibility near the distal end 20 and a steady transition between the stiff catheter shaft 12 and the flexible tip 16. Further, because the reinforcing section 32 is continuous and uninterrupted under the fill section 35, the flexibility of the medical catheter 10 is enhanced without compromising the torsional strength of the catheter shaft 12. Additionally, because the fill section 35 is affixed to the continuous reinforcing section 32, the fill section 35 is less likely to disengage from the medical catheter 10 during use in the vessel 24.

The length and thickness of the fill section 35 can be adjusted, as desired, to vary the flexibility of the catheter shaft 12. In the embodiment illustrated in FIGS. 1 and 2, the length and thickness of fill section 35 correspond to the groove length 46 and groove depth 48 so that the fill section 35 fills the groove 18 and does not disrupt the profile of the medical catheter 10. Although, for example, the thickness of the fill section 35 can be lesser than that of the groove depth 48.

In the embodiments illustrated in FIGS. 1 and 2, the fill section 35 includes a tubular shaped proximal fill component 52 and a tubular shaped distal fill component 54. To provide a steady transition between the stiff catheter shaft 12 and the flexible tip 16, the proximal fill component 52 has a hardness that is greater than that of the distal fill component 54 and less than that of the outer shell 34. Similarly, the distal fill component 54 has a hardness that is greater than that of the flexible tip 16 and less than that of the proximal fill component 52.

Materials for the fill components 52 and 54 may include, but are not limited to, nylon or blends thereof. The fill components 52 and 54 can be manufactured, for example, by extrusion. One suitable material of the fill components 52 and 54 is nylon 12, sold under the trademark VESTAMID™ by Creanova (Somerset, N.J.). For the embodiments illustrated in FIGS. 1 and 2, the proximal fill component 52 has a hardness of about 62 D, whereas the distal fill component 54 has a hardness of about 40 D. However, the material and hardness of the proximal fill component 52 and the distal fill component 54 can be varied to adjust the flexibility and strength of the transitional region 21. Additionally, the length of each fill component 52 and 54 can also be varied to adjust the flexibility and strength of the transitional region 21. Moreover, additional fill components (not shown) can be added to change the flexibility along the transitional region 21.

Figure 4B:
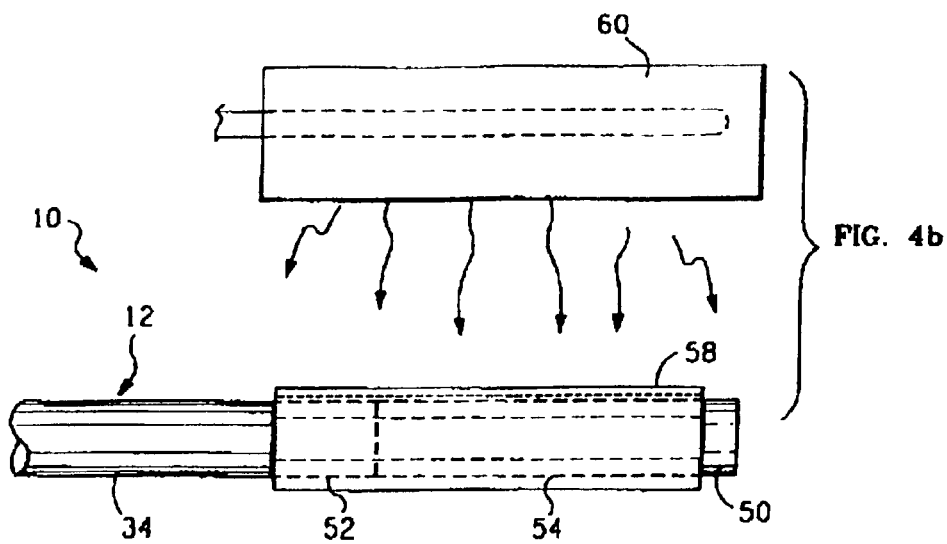
FIG. 4b is an enlarged side plan assembly view of a portion of the catheter shaft and a heat source.

FIG. 4a illustrates the proximal fill component 52 and the distal fill component 54 prior to positioning in the groove 18. FIG. 4a also illustrates a tubular shaped sleeve 58 that can be used to attach the fill components 52 and 54 to the catheter shaft 12. FIG. 4b illustrates the proximal fill component 52 and the distal fill component 54 positioned in the groove 18. Additionally, FIG. 4b illustrates the sleeve 58 positioned over the fill components 52 and 54 and a heat source 60. The sleeve 58 can be a shrink tube that is heated above the glass transition temperature of the fill components 52 and 54. Upon the application of heat from the heat source 60, the heated sleeve 58 shrinks to melt and force the fill components 52 and 54 into the groove 18. Subsequently, the sleeve 58 is cut away from the catheter shaft 12.

As provided above, the remaining shell segment 50 reduces or prevents unwrapping of the reinforcing section 32. However, after the fill section 35 is added to the groove 18, the fill section 35 prevents the reinforcing section 32 from unwrapping. Thus, the remaining shell segment 50 can be removed from the catheter shaft 12 prior to attaching the flexible tip 16.

Figure 5:
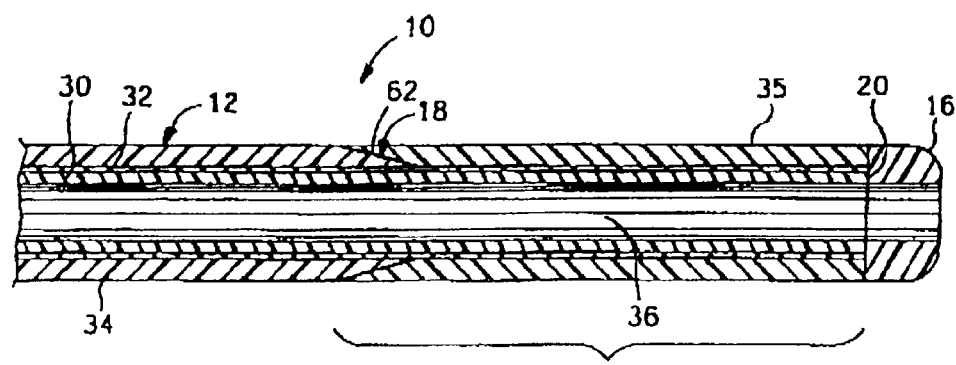
FIG. 5 is an enlarged cutaway view of a portion of another embodiment of the medical catheter.

FIG. 5 illustrates a portion of another embodiment of a medical catheter 10. More specifically, in this embodiment, the groove 18 is again primarily annular shaped. In this embodiment, however, the groove 18 includes a tapered area 62 positioned away from the distal end 20. The tapered area 62 provides a steady transition between the stiff catheter shaft 12 and the flexible tip 16. Further, in the embodiment illustrated in FIG. 5, the fill section 35 can be tubing having a thickness that is decreased near the tapered area 62. Thus, the flexibility of the catheter shaft 12 near the distal end 20 can be easily altered by changing the size of the tapered area 62 and the hardness of the fill section 35.

Figure 6:
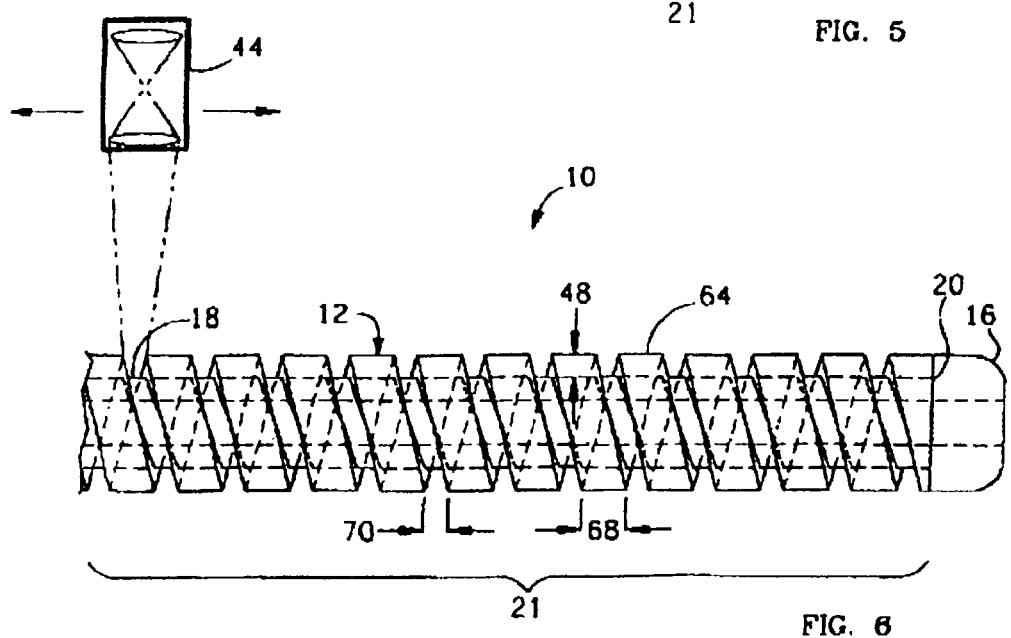
FIG. 6 is an enlarged perspective view of a portion of yet another embodiment of the medical catheter.

FIG. 6 illustrates a portion of another embodiment of a medical catheter 10. More specifically, in this embodiment, the groove 18 is helical or spiral shaped. As a result thereof, the transitional region 21 of the catheter shaft 12 includes a spiral shaped ridge 64 that is shaped somewhat similar to threads. In this embodiment, the groove depth 48 and a ridge pitch, a ridge width 68, and a ridge gap 70 can be varied along the transitional region 21 to precisely control the flexibility along the transitional region 21 of the medical catheter 10. For example, the ridge width 68 can be progressively decreased towards the distal end 20 to provide a transitional region 21 that is progressively softer and prevents or reduces kinking. Thus, the flexibility of the catheter shaft 12 near the distal end 20 can be easily altered by changing the ridge pitch, the ridge width 68, and/or ridge gap 70. Additionally, a fill material (not shown) can be added to some or all of the groove 18 to further control the flexibility.

Alternately, for example, a plurality of annular grooves (not shown) that are spaced apart can be utilized instead of the single helical shaped groove 18 illustrated in FIG. 6. For embodiments with a plurality of grooves, each of the grooves can have a relatively small groove width.

The reinforcing section 32 is continuous along the catheter shaft 12 and the transition region 21. As a result thereof, the medical catheter 10 provided herein has improved tracking and torsional characteristics within the vessel and the medical catheter 10 is relatively easy to manipulate by the physician. Moreover, the transitional region 21 is relatively easy and inexpensive to manufacture.

The distal end portion of the catheters of the present invention comprises a radiopaque segment 80. The radiopaque segment 80 may also be localized to the tip of the catheter, such as in the flexible tip 16. In other embodiments, the radiopaque segment 80 is present in both the distal end portion and the tip of the catheter. The radiopaque segment 80 may be localized in a single region of the catheter shaft 12, such as in a linear pattern, to promote full coverage of the liner 30. Alternately, the radiopaque segment 80 may be localized in separate regions to form a plurality of radiopaque locations within the radiopaque segment 80. The radiopaque location(s) within the radiopaque segment 80 can be oriented in any manner. For example, the radiopaque location(s) can be oriented in longitudinal strips or in circumferentially arranged rings around the catheter shaft 12. In some embodiments, a plurality of rings (e.g., two or more) of the same or varying widths can be spaced by known distances, thus functioning as a marker for measuring, among other things, lesion length. The pattern in which the radiopaque material is applied, however, is not particularly important, but rather that the radiopaque material is applied between the inner liner 30 and the outer shell 34. In some embodiments, the catheter comprises a radiopaque segment 80 that comprises one or more radiopaque braid filaments, one or more bands, longitudinal continuous or discontinuous band(s), or dots. In other embodiments, the radiopaque material can be deposited in a pattern or verbiage showing the catheter's manufacturer, size, curve style, and the like. In some embodiments, the outer shell 34 of the radiopaque segment 80 comprises a material having properties that are different from those of the inner liner 30 to form, for example, a soft distal segment.

Applying the radiopaque material between the inner liner 30 and outer shell 34, as opposed to incorporating it into the polymer fill that the catheter comprises, provides increased or improved properties of the catheter. Such increased or improved properties of the catheter include, for example, retention of the elastomeric properties, structural integrity, and tensile strength of the catheter, which are compromised when the radiopaque material is incorporated into the polymer forming the inner liner 30 and/or the outer shell 34.

The radiopaque segment 80 of the catheter comprises a radiopaque material. Radiopaque materials are well known to those skilled in the art. Radiopaque materials include, but not limited to, stainless steel, gold, tantalum, platinum, bismuth, iridium, zirconium, iodine, titanium, barium, silver, tin, tungsten, bromide, alloys of these materials, salts of these materials, or any combination thereof. In some embodiments, the radiopaque material is barium sulfate, bismuth trioxide, bismuth subcarbonate, or Tantalum Powder-Type 268/1905 ZM-414 (-325 Mesh size) distributed by Fansteel Metals. The radiopaque material can also be ceramic including, but not limited to, zirconia, alumina, zirconium nitrate, titanium nitrite, graphite, pyrolytic carbon, or other ceramics. In some embodiments, the radiopaque material is in an ink, paste, or powder form. It is well known to make paintable radiopaque materials (see, for example, U.S. Pat. No. 4,629,451 and Spurlock et al., *Online Journal of Veterinary Research*, 4(1): pp 106-123, each of which is incorporated herein by reference in its entirety).

In some embodiments, the tubular catheter shaft 12 comprises unfilled or low-loaded inner liner 30 and/or outer shell 34. For example, the inner liner 30 and outer shell 34 each, independently, may include a radiopaque material and/or filler and/or colorant, such that the total content of the radiopaque material and/or filler and/or colorant in inner liner 30 and/or outer shell 34 is between about 0.1% and about 10%, or between about 0.1% and about 5%, or between about 0.1% and about 2% of the total weight making up the inner liner 30 and/or outer shell 34. In some embodiments, the inner liner 30 and outer shell 34 each, independently, may exclude a radiopaque material and/or filler and/or colorant, thus having 0% by weight of the total weight making up the inner liner 30 and/or outer shell 34. An unfilled inner liner 30 and/or outer shell 34 have the advantages of retaining mechanical integrity and modulus of elasticity.

In some embodiments, the outer shell 34 is ablated at the distal end portion of the catheter, thus revealing the inner liner 30 and, optionally, the reinforcing section 32. Ablation techniques for removing a portion of the outer shell 34 of the catheter while leaving the inner liner 30 intact are well known to those skilled in the art. For example, laser ablation techniques are described in U.S. Pat. No. 6,059,769, which is incorporated herein by reference in its entirety. Alternately, the distal end portion of the catheter can be completely masked with, for example, alkaline or acid resistant mask material (i.e., Microstop, polyesters, acrylic, wax, etc.). The type of mask material depends on the coating process to follow. The mask can be removed from the outer shell 34 using a laser, sandblaster, or other appropriate method. Any pattern can be made by selectively removing mask material from the outer shell 34. The exposed surface (non-masked areas) can then be coated with radiopaque material by, for example, the processes described below. Other masking techniques are also possible (i.e., physical, chemical, or mechanical). The radiopaque material can then be applied over the inner liner 30 and over the reinforcing section 32, if present.

The radiopaque material can be applied to a catheter by any of a number of processes known by those skilled in the art. The radiopaque material can be applied by, for example, dipping, spraying, painting, electroplating, plasma vapor deposition, cathodic arc deposition, sputtering, laser welding or fusing, resistance welding, ion beam assisted deposition, ion implantation, pad printing, or any combination thereof. The thickness of the radiopaque material on the catheter can be about 50 microns or less. In some embodiments, the thickness of the radiopaque material can be about 25 microns or less, or about 10 microns or less.

Material comprising the outer shell 34 may be re-applied over the radiopaque material. Application of the outer shell material can be accomplished by methods well known to those skilled in the art. For example, the outer shell material can be applied by the same methods used for installing fill components 52 and 54 for filling groove 18, as described above. The process for applying the outer shell material depends upon numerous factors that can include the type of material comprising the outer shell 34.

By applying the radiopaque material over the inner liner rather than incorporating it into the polymer fill that the catheter comprises allows the catheter to have thinner walls. A thinner catheter also allows for an increase in the lumen. Alternatively, the lumen can remain the same size and the overall diameter of the catheter can be decreased, thus allowing delivery of a smaller catheter with an accompanying smaller puncture site in the individual being catheterized. Further, applying the radiopaque material between the inner liner 30 and outer shell 34, as opposed to incorporating it into the polymer fill that the catheter comprises, provides increased or improved properties of the catheter. Such increased or improved properties of the catheter include, for example, retention of the elastomeric properties, structural integrity, and tensile strength of the catheter, which are compromised when the radiopaque material is incorporated into the polymer forming the inner liner 30 and/or the outer shell 34.

While the particular medical catheter 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A medical catheter adapted for use within a body vessel, the medical catheter comprising:
   a tubular catheter shaft having a distal end that fits within the body vessel, the catheter shaft comprising an inner liner and an outer shell; the inner liner and the outer shell comprising no radiopaque material or comprising between 0.1 and 10% by weight of radiopaque material;

a radiopaque segment consisting of a radiopaque ink, or a radiopaque powder, or a radiopaque paste applied between the inner liner and outer shell to form the radiopaque segment; and a reinforcing section between the inner liner and outer shell.

2. The medical catheter of claim 1 wherein the reinforcing section comprises a tubular braid.

3. The medical catheter of claim 2 wherein the radiopaque segment is embedded within the braid.

4. The medical catheter of claim 1 wherein the radiopaque segment is localized to a tip of the catheter.

5. The medical catheter of claim 1 wherein the outer shell around the radiopaque segment comprises a material having properties that are different from those of the inner liner within the radiopaque segment.

6. The medical catheter of claim 5 wherein the outer shell around the radiopaque segment forms a soft distal segment.

7. The medical catheter of claim 1 wherein the radiopaque segment forms a circumferential ring around the inner liner.

* * * * *